United States Patent
Pichard et al.

(10) Patent No.: US 9,267,885 B2
(45) Date of Patent: Feb. 23, 2016

(54) SMOKE DETECTION CIRCUIT, SMOKE DETECTOR COMPRISING SAID CIRCUIT AND ALARM DEVICE COMPRISING BOTH THE CIRCUIT AND THE DETECTOR

(75) Inventors: Laurent Pichard, Nanterre (FR); Stephane Di Marco, Nanterre (FR)

(73) Assignee: FINSECUR, Nanterre (FR)

( * ) Notice: Subject to any disclaimer, the term of this patent is extended or adjusted under 35 U.S.C. 154(b) by 247 days.

(21) Appl. No.: 13/823,467

(22) PCT Filed: Sep. 14, 2011

(86) PCT No.: PCT/FR2011/052102
§ 371 (c)(1), (2), (4) Date: Mar. 14, 2013

(87) PCT Pub. No.: WO2012/035259
PCT Pub. Date: Mar. 22, 2012

(65) Prior Publication Data
US 2013/0176131 A1     Jul. 11, 2013

(30) Foreign Application Priority Data
Sep. 14, 2010   (FR) ..................................... 10 57338

(51) Int. Cl.
*G08B 17/10* (2006.01)
*G01N 21/53* (2006.01)
*G08B 17/107* (2006.01)
*G08B 29/04* (2006.01)

(52) U.S. Cl.
CPC .............. *G01N 21/53* (2013.01); *G08B 17/107* (2013.01); *G08B 29/043* (2013.01); *Y10T 29/4913* (2015.01)

(58) Field of Classification Search
CPC ................................ G08B 17/10; G01N 21/53
USPC ........................................................... 340/630
See application file for complete search history.

(56) References Cited

U.S. PATENT DOCUMENTS

| 4,616,928 A | * | 10/1986 | Leavitt et al. | .................. 356/338 |
| 5,138,302 A | | 8/1992 | Nagaoka et al. | |
| 5,451,931 A | * | 9/1995 | Muller et al. | .................. 340/630 |

(Continued)

FOREIGN PATENT DOCUMENTS

| EP | 1 253 566 A2 | 10/2002 |
| WO | WO-81/01765 | 6/1981 |

(Continued)

*Primary Examiner* — Jennifer Mehmood
*Assistant Examiner* — John Mortell
(74) *Attorney, Agent, or Firm* — IM IP Law PLLC; C. Andrew Im (57) ABSTRACT

The optical scattering-based smoke detector comprises a scattering zone accessible to the smoke, a printed circuit forming a supporting member and a first and second light reflectors mounted on a common supporting member. An electronic smoke detection unit, a light emitter and a light receiver are mounted on the printed circuit. The receiver is sensitive to at least some of the wavelengths of the light rays emitted by the emitter. The first light reflector facing the emitter to direct the emitted light into a detection zone in the scattering zone. The second light reflector facing the receiver to direct, in the presence of smoke in the scattering zone, the scattered light from the detection zone onto the receiver. A single mechanical part comprises the first and second light reflectors and a link resistant to the passage of the light from the first light reflector to the second light reflector.

16 Claims, 7 Drawing Sheets

(56) References Cited

U.S. PATENT DOCUMENTS

| | | | |
|---|---|---|---|
| 6,288,647 B1 * | 9/2001 | Yamano | 340/630 |
| 6,320,190 B1 * | 11/2001 | Voevodin | 250/338.5 |
| 2002/0089426 A1 * | 7/2002 | Qualey et al. | 340/628 |
| 2008/0252468 A1 | 10/2008 | Mueller et al. | |
| 2008/0297361 A1 * | 12/2008 | Cole et al. | 340/630 |
| 2010/0328085 A1 | 12/2010 | Bohanon | |

FOREIGN PATENT DOCUMENTS

| | | |
|---|---|---|
| WO | WO-00/72282 A1 | 11/2000 |
| WO | WO-2009/036988 A1 | 3/2009 |

* cited by examiner

SMOKE DETECTION CIRCUIT, SMOKE DETECTOR COMPRISING SAID CIRCUIT AND ALARM DEVICE COMPRISING BOTH THE CIRCUIT AND THE DETECTOR

RELATED APPLICATIONS

This application is a §371 application from PCT/FR2011/052102 filed Sep. 14, 2011, which claims priority from French Patent Application No. 1057338 filed Sep. 14, 2010, each of which is herein incorporated by reference in its entirety.

TECHNICAL FIELD OF INVENTION

This invention concerns a smoke detection circuit, a smoke detector comprising said circuit and an alarm device comprising both the circuit and the detector. It applies, in particular, to detecting smoke in residential, industrial commercial or recreational buildings and public or private works structures.

BACKGROUND OF THE INVENTION

Many smoke detectors are known. The principle of an optical scattering-based smoke detector, for example, is based on utilizing, firstly, an emitter of light rays and, secondly, a receiver of light signals scattered by the ambient air. When there is no smoke in the air that enters the detector, the receiver only receives a very small amount of the scattered light. In contrast, when there is smoke in the air that enters the detector, this scatters the light from the emitter and thus lights the receiver.

To realize such smoke detectors, every emitter (typically a light-emitting diode) and receiver (typically a photodiode or phototransistor) component is positioned obliquely on a printed circuit, forming an angle of angle of approximately 35 to 45 degrees with this printed circuit.

However, the positioning of these components, which is very difficult to realize and test, is the main cause of manufacturing faults in the detectors and imposes high manufacturing costs. Faulty positioning can cause either a parasitic reflection blinding the receiver component or a reduction in sensitivity. In addition, the positioning of these components is not very reproducible, reducing the ability to establish a precise specification for the smoke detectors that comprise them. Lastly, the wires than connect these components to the printed circuit act as antennas collecting parasitic signals, thus reducing the detector's sensitivity.

In order to reduce these parasitic effects, document U.S. Pat. No. 5,138,302 proposes replacing the receiver by a component mounted directly on the printed circuit and collecting the light scattered by the smoke particles by using a lens positioned close to the receiver. However, in the proposed device the emitter comprises connecting wires to the printed circuit; this causes many drawbacks, for example, difficulty in correctly adjusting the angle between the emitted beams and the receiver's axis, the existence of an antenna effect towards the printed circuit likely to bring parasites to it, or the impossibility of properly defining the interaction zone. The problems mentioned above are therefore still to be resolved.

Ultimately, a significant portion of the circuit production is rejected before the detector is assembled, even when it is not the complete detector that is rejected during a test.

In addition, the problem of positioning the emitter and receiver components makes it difficult to utilize surface-mounted components ("SMC") since they are miniaturized and therefore more sensitive to faulty positioning.

Document WO 2009/036988 is also known; it presents a radiation guide that can be surface-mounted, designed to be mounted on an emitter of light rays. However, the mechanical positioning of this radiation guide is still a problem and faulty positioning can lead to low sensitivity of the detector comprising two such radiation guides facing, respectively, an emitter and a receiver. The mechanical assembly of two guides requires the realization of a complex, therefore costly, part in which parasitic rays can go from the emitter to the receiver and hamper detection.

OBJECT AND SUMMARY OF THE INVENTION

This invention aims to remedy all or part of these drawbacks.

To this end, according to a first aspect, this invention envisages an optical scattering-based smoke detector that comprises:

a scattering zone accessible to the smoke;

a printed circuit forming a supporting member and on which an electronic smoke detection unit is mounted;

a light emitter mounted on said printed circuit;

a light receiver, sensitive to at least a portion of the wavelengths of the light rays emitted by the emitter and mounted on said printed circuit;

a first light reflector facing the emitter so as to direct the light emitted by the emitter into a detection zone in the scattering zone; and a second light reflector facing the receiver so as to direct, if there is smoke in the scattering zone, the scattered light coming from said detection zone onto the receiver;

wherein a single mechanical part comprises the first and second light reflectors and a link resistant to the passage of the light from the first light reflector to the second light reflector.

Thanks to these provisions, positioning the light emitter and receiver components is performed at the same time. It is therefore simplified and the reproducibility of the electronic smoke detection circuit's sensitivity is improved. Reproducibility of the emission/reception angles of the light rays is also improved. The production of light reflectors is made easier since they can be molded conjointly to the link connecting them.

Another problem that arises in optical detectors relates to the detection of faults and in particular the absence of emission by the light emitter component and/or where there is a loss of sensitivity in a light receiver component. However these faults are critical since they limit, even prevent, the detection of smoke.

In particular embodiments, said link comprises an optical guide designed to carry a portion of the light emitted by the emitter to the receiver, the electronic smoke detection unit being designed to detect the absence of reception, by said receiver, of said portion of the light emitted by the emitter and to emit a signal representative of this absence of reception.

Thanks to these provisions, a very small portion of the light emitted by the emitter continuously arrives at the receiver. When it is detected that the receiver is no longer emitting a signal representative of this portion or is emitting an attenuated signal, the electronic unit signals a detector fault or malfunction. The portion of the light that arrives continuously is calibrated to always be lower than the level of light required for detecting smoke so that this permanent portion does not disrupt the detection of smoke.

In embodiments, the link resistant to the passage of the light is a split optical guide, a portion of the split optical guide emerging at the exterior of the optical detector.

Thanks to these provisions, it is possible to:

check the operation of the emitter component by positioning an external receiver component, e.g. a movable casing, opposite the place where said optical guide emerges, especially in the case where the emitter component is likely to emit in the visible field, communicate at least one item of information to the outside such as, for example, signal a detection of smoke or a failure of the smoke detector circuit and/or communicate with the smoke detection circuit through the emission, for example via a remote control, of a light signal to the place where said optical guide emerges.

In particular embodiments, the link resistant to the passage of the light is a split optical guide, one optical guide forming a chicane, one optical guide comprising a zone absorbing light in the wavelengths of the light rays emitted by the emitter and/or one optical guide comprising a zone reflecting light in the wavelengths of the light rays emitted by the emitter.

Thanks to these provisions, the risks of parasitic lighting of the receiver via the optical fiber are reduced.

In particular embodiments, the link resistant to the passage of the light bears a centering stud.

Thanks to these provisions, the positioning of the single part comprising the prisms is reproducible and precise.

In particular embodiments, the light emitter emits light rays with wavelengths in the infrared spectrum and at least one prism is made of polycarbonate.

Thanks to these provisions, the receiver is not sensitive to ambient light, which reduces the risks of a false alarm and the transmission of light rays is facilitated both in the prism on the light emitter side and in the prism on the light receiver side.

In particular embodiments, the first light reflector comprises a convergent reflector arranged to focus the light in the detection zone and/or the second light reflector comprises a convergent reflector arranged to focus the light from the detection zone onto the receiver.

Thanks to these provisions, the detection zone, where the light rays pass through any smoke to be detected, is smaller, reducing the risks of parasitic reflection and the noise level.

In particular embodiments, at least one reflector consists of one surface of an optical prism and another surface of said optical prism is substantially parallel to the plane of the printed circuit.

Thanks to these provisions, the positioning of the light reflector is thus easy since the surface of the prism parallel to the plane of the printed circuit and facing one of the emitter or receiver components is easy to position.

In particular embodiments, at least one prism bears a centering stud. Thanks to these provisions, the positioning of the prisms over a series of optical detectors is reproducible.

In particular embodiments, the optical detector further comprises:

a casing for housing the optical detector, arranged to allow air to pass through the scattering zone while minimizing the introduction of parasitic light into said scattering zone; and an intermediate supporting member placed in the casing that delimits a circuit zone, which houses the printed circuit, and the scattering zone, the intermediate supporting member being provided with an optical wall arranged so that, if there is no smoke in the scattering zone, the light emitted by the emitter is prevented from reaching the receiver.

In particular embodiments, at least one of the emitter and receiver of light is a surface-mounted component ("SMC").

Thanks to these provisions, the printed circuit's surface area is smaller and all the electronic components borne by the printed circuit can be SMCs, which reduces the printed circuit's cost of components and manufacturing.

In particular embodiments, the printed circuit comprises a ground plane serving as electromagnetic protection for the light receiver component.

Thanks to these provisions, the need for a metal skeleton on this component or in a smoke detector's casing is reduced, or even removed.

According to a second aspect, this invention envisages an alarm device comprising at least one smoke detector that is the subject of this invention, and an emitter of alarm signals, where the emission of alarm signals is representative of the detection of smoke by a said smoke detector.

According to a third aspect, this invention envisages a device for manufacturing two reflector prisms for a smoke detector device simultaneously, comprising an injection cylinder and a polymer injection mold, characterized in that said injection mold comprises at least one feed channel linking the nose of an injection cylinder and the mold inlet, said inlet being located in the area of the mold that corresponds to a link between the two prisms.

In particular embodiments, said inlet is located in the central portion of the area of the mold that corresponds to a link between the two prisms.

According to a fourth aspect, this invention envisages a method of manufacturing an optical scattering-based smoke detector, which comprises:

a step of injecting polymer into an injection mold, said injection mold comprising at least two zones for forming two prisms and a feed channel linking the nose of an injection cylinder and the mold inlet, said inlet being located in the area of the mold that corresponds to a link between the two prisms and a step of mounting the molded part comprising the two prisms and the link between the prisms on a printed circuit forming a supporting member and comprising, facing one of said prisms, a light emitter and, facing the other of said prisms, a light receiver sensitive to at least one portion of the wavelengths of the light rays emitted by the emitter.

In particular embodiments, during the injection step, first of all a polymer is injected that is at least partially transparent to the wavelengths utilized by the emitter and the receiver, then a polymer more opaque to said wavelengths is injected.

Thanks to each of these provisions, the material forming the injection sprue is used; this, firstly, avoids wasting polymer and, secondly, makes it possible to eliminate a deflashing operation when mechanical parts are unmolded. In this way two savings are realized.

According to a fifth aspect, this invention envisages a method of manufacturing a smoke detector, comprising a manufacturing step according to the fourth aspect of the invention; a step of mounting the electronic smoke detection unit, the emitter and the receiver on the printed circuit through automatic soldering by a surface component soldering machine; a step of mounting the mechanical part on the intermediate supporting member; and a step of positioning the printed circuit and the intermediate supporting member in the casing.

A sixth aspect of the invention envisages a manufacturing appliance for implementing the manufacturing method according to the fifth aspect of the invention.

As the particular characteristics, advantages and aims of this alarm device, of these methods and of these manufacturing devices are similar to those of the smoke detector that is the subject of this invention they are not repeated here.

BRIEF DESCRIPTION OF THE DRAWINGS

Other advantages, aims and characteristics of the present invention will become apparent from the description that will follow, made, as an example that is in no way limiting, with reference to the drawings included in an appendix, in which.

DETAILED DESCRIPTION OF EMBODIMENTS

For reasons of clarity, the figures are not to scale.

Figure 1:
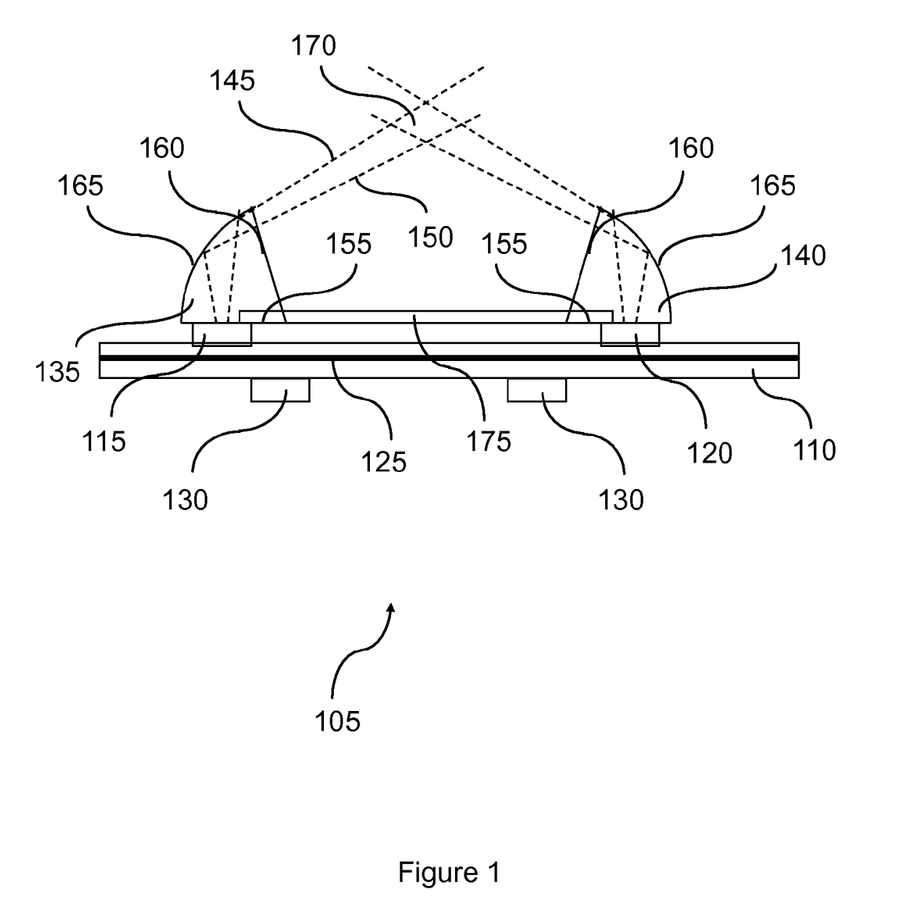
FIG. 1 represents, schematically and in cross-section view, a smoke detection circuit and light guides according to a particular embodiment of this invention.
Figure 2:
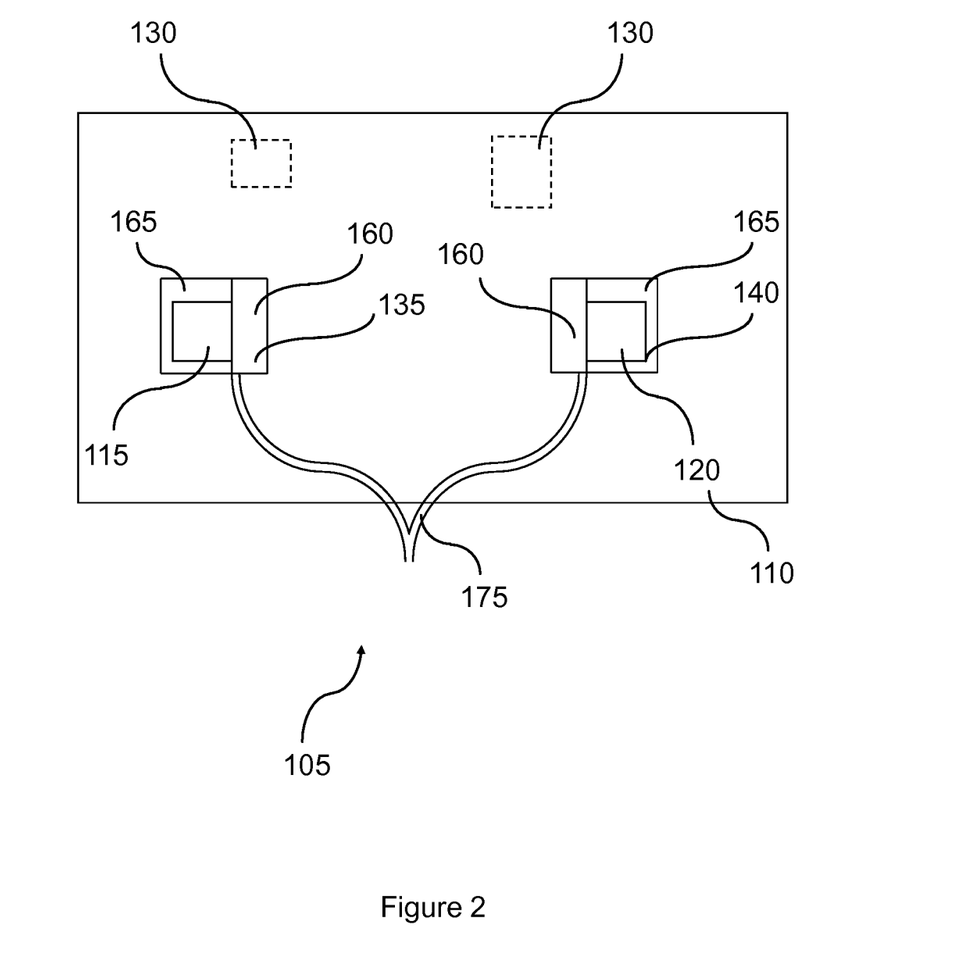
FIG. 2 represents, schematically and in a top view, the smoke detection circuit shown in FIG. 1.

FIGS. 1 and 2 show a smoke detection circuit 105 comprising a printed circuit 110 bearing a light emitter component 115, a light receiver component 120, a ground plane 125 and supply and signal processing components 130. The printed circuit 110 is of known type and designed to bear surface-mounted components, SMCs. These components have the advantage of being able to be mounted and soldered automatically onto the printed circuit using automatic soldering machines. The SMC-type emitter and receiver have their optical axes substantially parallel to each other and substantially perpendicular to the printed circuit. The ground plane 125 is a metal plane inserted into the mass or on the surface of the printed circuit 110. In the embodiment described, this ground plane 125 forms a protection against electromagnetic emissions for at least the light receiver component 120.

Two light reflectors, formed here of the surfaces 165 of two prisms 135 and 140, are positioned facing the emitter 115 and receiver 120 components. The prism 135 facing the emitter 115 is arranged to direct the light emitted by the emitter 115 into a detection zone 170; and the prism 140 facing the receiver 120 is arranged so as to direct, in the presence of smoke in the detection zone 170, the scattered light coming from said detection zone 170 onto the receiver 120. The intersection of the emitted light cone and the usable reception cone defines a zone 170, called a detection zone.

Light rays 145 and 150, usable for detecting smoke, and the detection zone 170 are shown by dashed lines in FIG. 1. Each of prisms 135 and 140 has a lower surface 155 substantially parallel to the plane of the printed circuit 105, an oblique flat side surface 160 and a curved surface 165 forming a convergent mirror.

The light emitter component 115 is, for example, a light-emitting diode operating in the infrared spectrum. The light receiver component 120 is, for example, a photodiode or phototransistor operating in the same wavelengths as the light emitter component 115. The supply and signal processing components 130 are designed to, firstly, supply electricity to components 115 and 120 and, secondly, to process the electrical signals output from the light receiver component 120 to determine whether smoke is crossing the detection zone 170. The components 130 and their connection are known to the person skilled in the art of smoke detectors and thus they are not described any further here.

Prisms 135 and 140 are, for example, made of polycarbonate. This material has the advantage of being, at least partially, transparent in part of the infrared spectrum. Thus, the receiver is not sensitive to ambient light, which reduces the risks of a false alarm and the transmission of light rays is facilitated both in the prism on the light emitter side and in the prism on the light receiver side. As shown in FIG. 1, the shape of the curved surface 165 of prisms 135 and 140 and the angle of incidence of the light rays 145 and 150 on this curved surface 165 make it a convergent mirror whose focal length is substantially equal to the distance traveled by the central light rays emitted by the light emitter component 115 before reaching the curved surface 165, multiplied by the optical index of the material the prism is made of.

In this way, the light rays output from the prism facing the light emitter component 135 are practically parallel.

For reasons of symmetry, the light rays from the detection zone 170 converge, thanks to the curved surface 165 of the prism facing the light receiver component 140, on the sensitive portion of this component 140.

Figure 3:
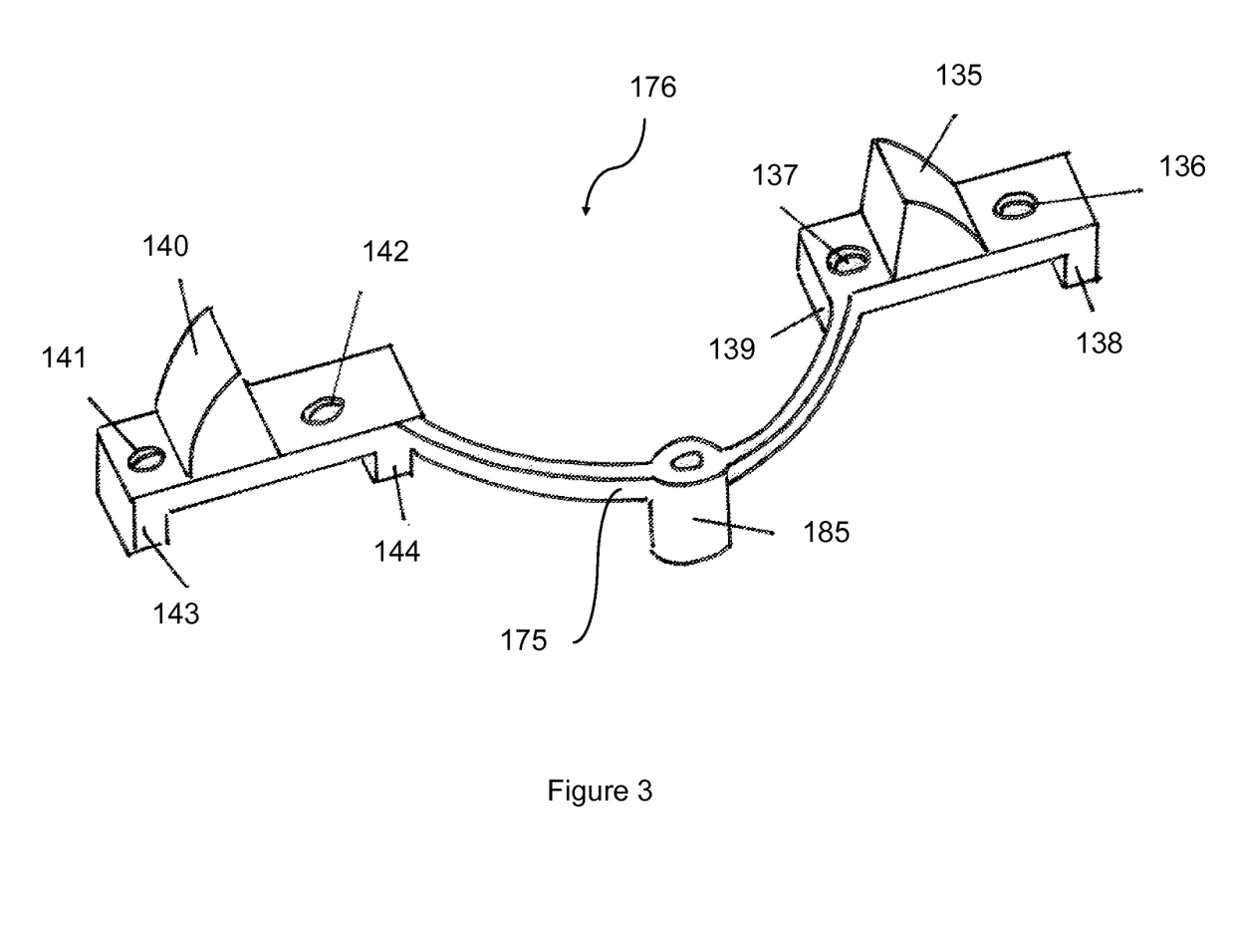
FIG. 3 represents a perspective view of a particular embodiment of the mechanical part comprising the prisms.

As shown in FIG. 2 and FIG. 3, the prisms 135 and 140 form a single mechanical part 176, with a link 175 connecting prisms 135 and 140 within this single part 175.

In particular embodiments, this link comprises an optical guide that carries a portion of the light emitted by the emitter to the receiver, the electronic smoke detection unit being designed to detect the absence of reception, by said receiver, of said portion of the light emitted by the emitter and to emit a signal representative of this absence of reception. Thus, a very small portion of the light emitted by the emitter arrives continuously at the receiver. When it is detected that the receiver is no longer emitting a signal representative of this portion or is emitting an attenuated signal, the electronic unit signals a detector fault or malfunction. The portion of the light that arrives continuously is calibrated (by means of the geometry of the mechanical part) to always be less than the level of light required for detecting smoke so that this permanent portion does not disrupt the detection of smoke.

Measuring the amount of light arriving continuously at the receiver thus allows the aging of the emitter and/or the receiver to be measured.

Either aging or a fault preferably cause a signal to be emitted, light, sound or to a central system, representative of the problem and of the need to carry out repair or maintenance operations on the smoke detector.

In other embodiments, the mechanical link forms a split optical guide 180 to prevent the parasitic light from the emitter component 115 reaching, by means of it, the receiver component 120. Thus, the first light reflector formed by a surface 165 of prism 135 is connected to the second light reflector, formed by a surface 165 of prism 140, by means of a link resistant to the passage of parasitic light to form a single mechanical part 176.

In other embodiments, the link between prisms 135 and 140 can be formed of any other means arranged so as to prevent parasitic light passing from the emitter to the receiver. For example the link can be formed by an optical guide comprising a central zone in the form of a chicane, a zone absorbing light in the wavelengths of the light rays emitted by the emitter and/or a zone reflecting light in the wavelengths of the light rays emitted by the emitter.

The mechanical part 176 can, advantageously, be obtained by injecting a polymer, for example polycarbonate, into a mold by positioning in the injection tool the hole through which the molten material penetrates the mold in the area corresponding to the central zone of the split optical guide 180. This makes it possible to use the injection sprue, formed by the material having filled the feed channel between the nose of the injection cylinder and the mold inlet, to produce the optical guide and thus to save material and avoid an additional operation, i.e. extracting the sprue, when the injected parts are retrieved. These injection techniques are known to the person skilled in the art of working polymers and thus they are not described any further here.

Figure 4:
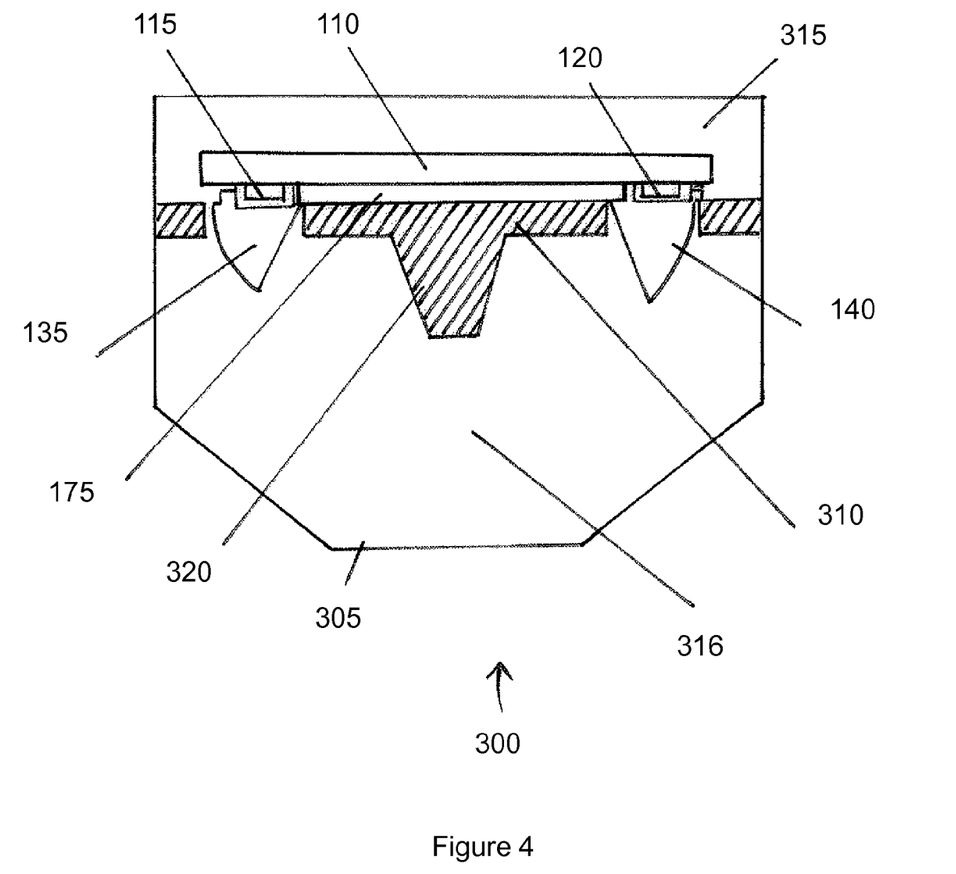
FIG. 4 represents, schematically and in a side view, a particular embodiment of the smoke detector that is the subject of this invention.

As shown in FIG. 4, in an embodiment of the invention, a smoke detector 300 comprises a casing 305, in which is placed the smoke detection circuit 105 and an intermediate supporting member 310 delimiting two zones in the casing 305, separated by the supporting member: a circuit zone 315 that houses the smoke detection circuit and a scattering zone 316 accessible to smoke particles. The casing 305 has openings in chicanes to allow air to pass through the scattering zone 316 while minimizing the penetration of ambient light into the scattering zone 316. The internal walls of the casing are arranged to reflect the light rays as little as possible. As shown in FIG. 4 the surface of the intermediate supporting member 310 on the scattering zone 316 side is provided with an optical wall 320 which, if there is no smoke in the scattering zone 316, prevents the light emitted by the emitter 115, towards the scattering zone 316 via prism 135, to reach the receiver 120 via prism 140. The optical wall 320 has two opposite surfaces 321, 322 that are crenelated to reflect the light rays as little as possible. The prism 135 facing the emitter 115 is positioned on one of the sides of the wall 320 and the prism 140 facing the receiver 120 is placed on the other side of the wall 320 such that the light rays cannot circulate directly from one prism to the other. Prism 135 facing the emitter 115 focuses the light into a spot just above the wall 120. When smoke particles are present in the detection zone 170 the light is scattered towards the prism 140 facing the receiver 120, which collects it and sends it towards the receiver 120.

In the embodiment shown in FIG. 3, FIG. 4, FIG. 5 and FIG. 6, the mechanical part 176 comprising the two prisms 135, 140 is mounted on the supporting member 310 such that the configuration of prism 135 in relation to prism 140 is fixed. The mechanical part 176 is provided with a device for precisely positioning the intermediate supporting member 310, namely centering studs designed to work with holes located on the intermediate supporting member 310, holes 141, 142, 136, 137 designed to work with pins located on the intermediate supporting member 310, or clips located on the intermediate supporting member 310. The positioning of the prisms is thus easily reproducible. This makes it possible to reproduce the emission/reception angles of the light rays.

Figure 5:
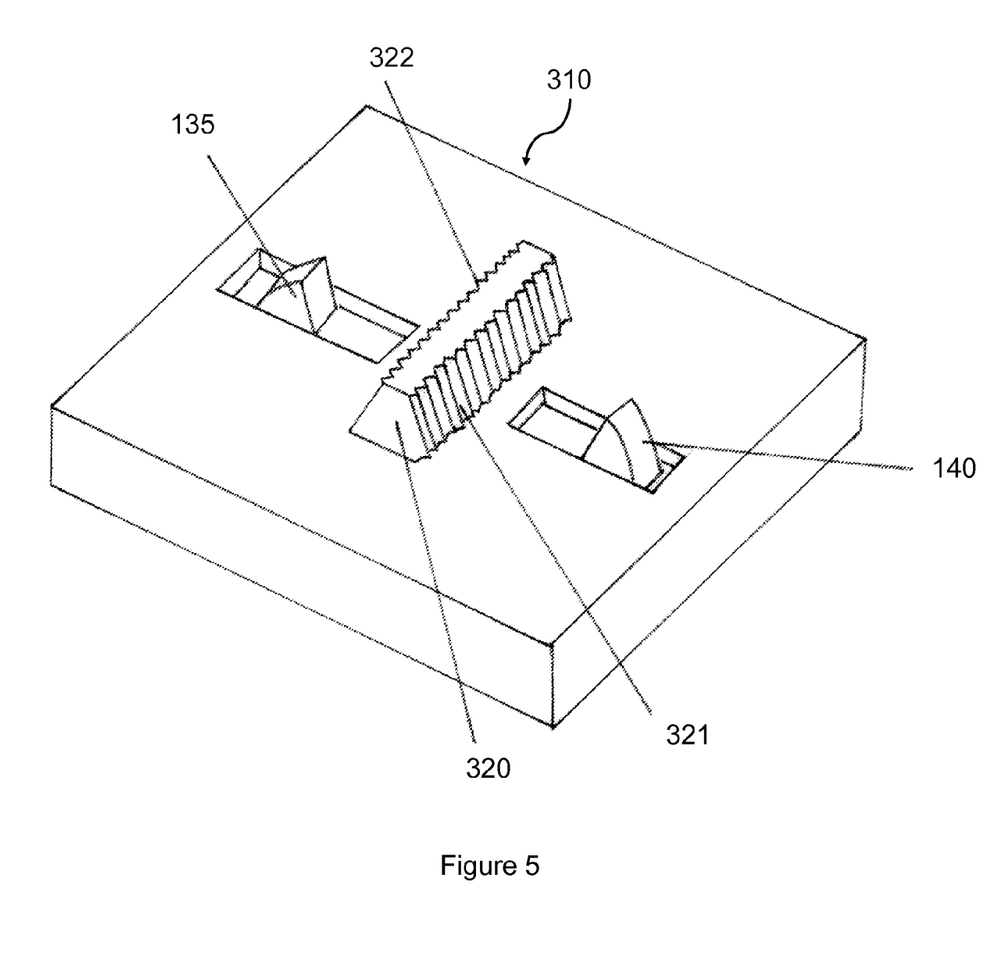
FIG. 5 represents a perspective view of a particular embodiment of the supporting member of the smoke detector.
Figure 6:
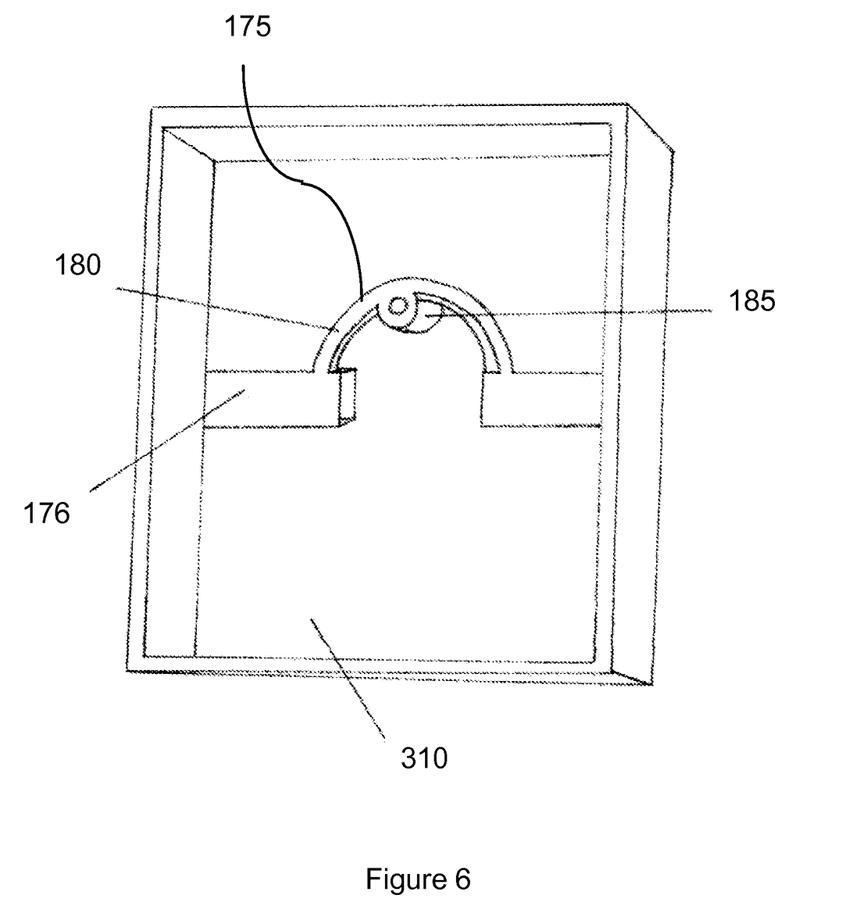
FIG. 6 represents a perspective view of the other side of the supporting member in FIG. 5

Two openings 1350, 1400 in the surface of the supporting member 310 allow the two prisms 135, 140 to be positioned in the scattering zone 116, the split optical guide 180 between the two prisms being positioned on the other side of the supporting member in the circuit zone 315. The supporting member 310 is arranged to prevent the parasitic light passing from the circuit zone 315 to the scattering zone, except through the prisms 135, 140.

On the surface located on the printed circuit side, it can be advantageous to equip prisms 135 and 140 with two flat undercuttings so as to allow the emitter 115 and receiver 120 to be positioned inside these undercuttings, the prisms can thus come into contact with the printed circuit.

In a variant, the prisms and/or the mechanical part can come into contact with the printed circuit by avoiding the above undercuttings but by providing stops 143, 144, 138 and 139.

In the embodiment shown in FIG. 4 the printed circuit 110 is fixed to the intermediate supporting member 310 by clips located, for example, on the periphery of this intermediate supporting member. In this way the optical prisms are precisely positioned with regard to the intermediate supporting member 310, which is itself precisely positioned with regard to the printed circuit 110. It is thus easy to reproduce the positioning of the prisms over a series of printed circuits.

In the embodiment shown in FIGS. 1 and 2, the optical fiber 180 emerges on the outside of the electronic smoke detection circuit.

Figure 7:
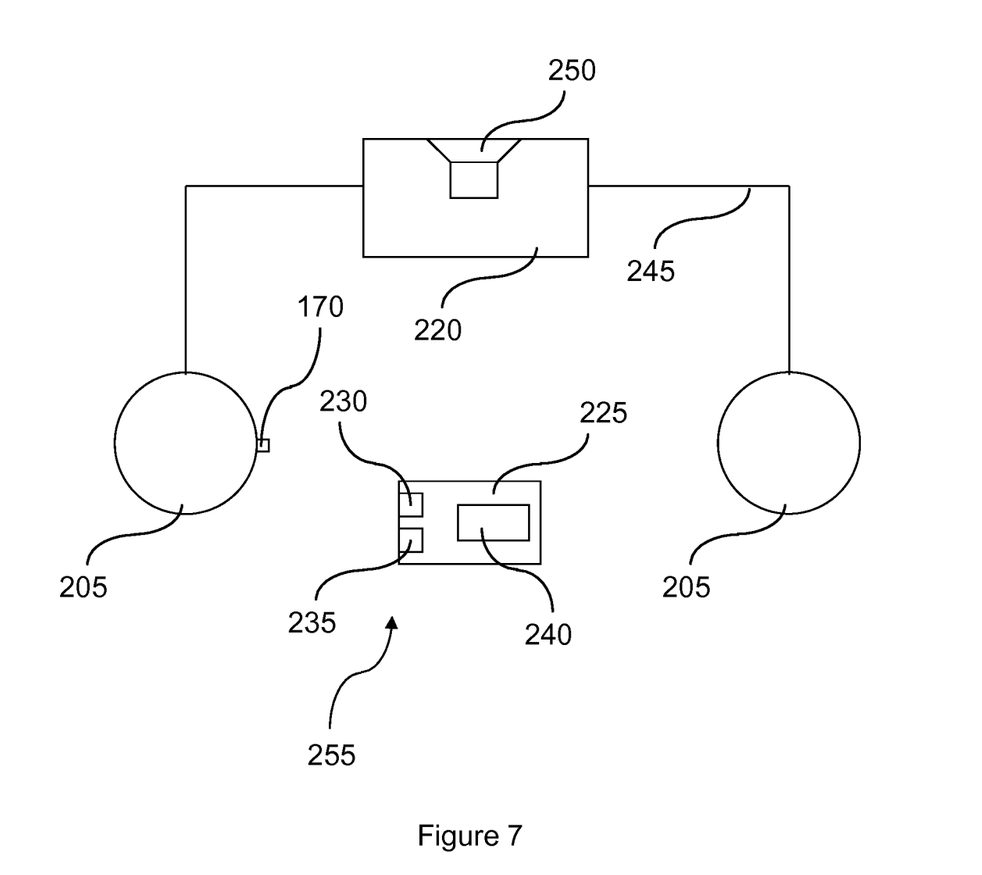
FIG. 7 represents, schematically and in a front view, a particular embodiment of an alarm device that is the subject of this invention.

In this way, it is possible to:

check the operation of the emitter component by positioning an external receiver component, e.g. a movable casing 225, shown in FIG. 7, opposite the place where the optical fiber 180 emerges, especially in the case where the emitter component is likely to emit in the visible band, communicate at least one item of information to the outside such as, for example, signal a detection of smoke or a failure of the smoke detector circuit visually or by means of a movable casing 225 and/or communicate with the smoke detection circuit by emitting, for example with a remote control 225 shown in FIG. 7, a light signal to the place where the optical fiber emerges.

As shown in FIG. 7, an alarm device 255 comprises at least one smoke detector 205 and, connected to each detector 205 by a link 245, wire or not, an emitter of alarm signals 220, where the emission of alarm signals is representative of the detection of smoke by a said smoke detector 205.

Here, the emitter of alarm signals 220 comprises a loudspeaker 250.

A movable casing 225, acting as remote control, comprises a light emitter 230 and a light receiver 235 able to be positioned facing the emergence of the optical fiber 180, and a circuit 240 controlling the light emitter 230 and the processing of electrical signals received by the light receiver 235.

This control circuit 240, for example a microprocessor running a computer program:

checks the operation of the emitter component, receives at least one item of information from the detection circuit 105, e.g. the state of its battery, the need for maintenance or the date of the last maintenance operation, or a failure of the smoke detector circuit and/or communicates with the smoke detection circuit 105, sending it a request or an instruction, e.g. for testing the connection 245 and triggering the emitter 220.

A particular method of manufacturing the mechanical part comprising prisms 135 and 140 consists of melting a polymer, e.g. polycarbonate, putting this in an injection cylinder and introducing it, through at least one feed channel, into a mold having the shape of the said mechanical part. Preferably, at least one such feed channel emerges in the zone corresponding to said light absorbing zone of this mechanical part.

Correlatively, a device for manufacturing the mechanical part comprising prisms 135 and 140 comprises a polymer, e.g. polycarbonate, injection mold comprising at least one feed channel linking the nose of the injection cylinder and the mold inlet, where this inlet is located in the zone that corresponds to the link between the two prisms and, preferably, in the central portion of this zone or in the portion corresponding to the light absorbing zone.

Thus, the material forming the injection sprue is used; this, firstly, avoids wasting polymer and, secondly, makes it possible to eliminate a deflashing operation when mechanical parts are unmolded. In this way two savings are realized.

Of course, the invention is not limited to the examples of realization described above and represented; from these other embodiments and forms of realization may be envisaged without in any way departing from the framework of the patent.

To manufacture an optical scattering-based smoke detector, that further comprises:

a casing for housing the optical detector, arranged to allow air to pass through the scattering zone while minimizing the introduction of parasitic light into said scattering zone; and an intermediate supporting member placed in the casing that delimits a circuit zone, which houses the printed circuit, and the scattering zone, the intermediate supporting member being provided with an optical wall arranged so that, if there is no smoke in the scattering zone, the light emitted by the emitter is prevented from reaching the receiver;

the following steps are implemented:

a step of injecting polymer into an injection mold, said injection mold comprising at least two zones for forming two prisms and a feed channel linking the nose of an injection cylinder and the mold inlet, said inlet being located in the area of the mold that corresponds to a link between the two prisms; preferably, first of all a polymer is injected that is at least partially transparent to the wavelengths utilized by the emitter and the receiver, then a polymer more opaque to said wavelengths is injected;

a step of mounting the electronic smoke detection unit, the emitter and the receiver on the printed circuit through automatic soldering by a surface component soldering machine;

a step of mounting the molded mechanical part comprising the two prisms and the link between the prisms on the intermediate supporting member and a step of positioning the printed circuit and the intermediate supporting member in the casing so that the light emitter is facing one of the prisms and the light receiver is facing the other prism.

The invention claimed is:

1. Optical scattering-based smoke detector, comprising:
   a scattering zone accessible to the smoke;
   a printed circuit forming a supporting member and on which an electronic smoke detection unit is mounted thereon;
   a light emitter mounted on said printed circuit;
   a light receiver mounted on said printed circuit, the receiver being sensitive to at least some of wavelengths of light rays emitted by the emitter;
   a first light reflector facing the emitter to direct the light emitted by the emitter into a detection zone in the scattering zone;
   a second light reflector facing the receiver to direct the light reflected by the first light reflector and scattered by the presence of smoke in the detection zone onto the receiver; and
   wherein a single mechanical part comprises the first and second light reflectors and a link resistant to the passage of the light from the first light reflector to the second light reflector.

2. Optical detector according to claim 1, wherein said link comprises an optical guide operable to carry a portion of the light emitted by the emitter to the receiver; and wherein the electronic smoke detection unit is operable to detect the absence of reception, by the receiver, of said portion of the light emitted by the emitter and to emit a signal representative of the absence of reception.

3. Optical detector according to claim 1, wherein the link resistant to the passage of the light is a split optical guide, a portion of the split optical guide emerging at the exterior of the optical detector.

4. Optical detector according to claim 1, wherein the link resistant to the passage of the light is a split optical guide, one optical guide forming a chicane and one optical guide comprising a zone absorbing light in the wavelengths of the light rays emitted by the emitter.

5. Optical detector according to claim 1, wherein the link resistant to the passage of the light is a split optical guide, one optical guide forming a chicane and one optical guide comprising a zone reflecting light in the wavelengths of the light rays emitted by the emitter.

6. Optical detector according to claim 1, wherein the link resistant to the passage of the light bears a centering stud.

7. Optical detector according to claim 1, wherein the light emitter emits light rays with wavelengths in an infrared spectrum; and wherein at least one light reflector is a prism made of polycarbonate.

8. Optical detector according to claim 1, wherein the first light reflector comprises a convergent reflector arranged to focus the light in the detection zone.

9. Optical detector according to claim 1, wherein the second light reflector comprises a convergent reflector arranged to focus the light from the detection zone onto the receiver.

10. Optical detector according to claim 1, wherein at least one light reflector comprises one surface of an optical prism.

11. Optical detector according to claim 10, wherein another surface of said optical prism is substantially parallel to the plane of said printed circuit.

12. Optical detector according to claim 10, wherein at least one optical prism bears a centering stud.

13. Optical detector according to claim 1, further comprising:
   a casing for housing the optical detector, arranged to allow air to pass through the scattering zone while minimizing the introduction of parasitic light into the scattering zone; and
   an intermediate supporting member placed in the casing that delimits a circuit zone, which houses said printed circuit and the scattering zone, wherein the intermediate supporting member being provided with an optical wall arranged, in the absence of smoke in the scattering zone, to prevent the light emitted by the emitter from reaching the receiver.

14. Optical detector according to claim 1, wherein at least one of the emitter and receiver is a surface-mounted component.

15. Optical detector according to claim 1, wherein said printed circuit comprises a ground plane serving as electromagnetic protection for the light receiver.

16. Alarm device comprising at least one optical scattering-based smoke detector according to claim 1 and an alarm emitter of alarm signals, wherein an emission of an alarm signal by the alarm emitter is representative of a detection of smoke by the optical detector.

* * * * *